(12) United States Patent
Harmon et al.

(10) Patent No.: US 9,782,539 B2
(45) Date of Patent: Oct. 10, 2017

(54) FLUID LEVEL MONITORING SYSTEM

(71) Applicants: Robert Lee Harmon, Long Beach, CA (US); Michael Parker, Camarillo, CA (US)

(72) Inventors: Robert Lee Harmon, Long Beach, CA (US); Michael Parker, Camarillo, CA (US)

(*) Notice: Subject to any disclaimer, the term of this patent is extended or adjusted under 35 U.S.C. 154(b) by 0 days.

(21) Appl. No.: 15/114,833

(22) PCT Filed: Feb. 6, 2015

(86) PCT No.: PCT/US2015/014928
§ 371 (c)(1),
(2) Date: Jul. 27, 2016

(87) PCT Pub. No.: WO2015/120342
PCT Pub. Date: Aug. 13, 2015

(65) Prior Publication Data
US 2016/0331894 A1    Nov. 17, 2016

Related U.S. Application Data

(60) Provisional application No. 61/937,963, filed on Feb. 10, 2014.

(51) Int. Cl.
*G08B 21/00* (2006.01)
*A61M 5/168* (2006.01)
*A61J 1/18* (2006.01)
*G01F 23/20* (2006.01)
*G08B 21/18* (2006.01)
*A61M 5/14* (2006.01)

(52) U.S. Cl.
CPC ............ *A61M 5/16845* (2013.01); *A61J 1/18* (2013.01); *G01F 23/20* (2013.01); *G08B 21/182* (2013.01); *A61J 2200/74* (2013.01); *A61J 2200/76* (2013.01); *A61M 5/1415* (2013.01); *A61M 2205/3553* (2013.01); *A61M 2205/3569* (2013.01); *A61M 2205/3592* (2013.01); *A61M 2205/50* (2013.01)

(58) Field of Classification Search
CPC ............ A61M 5/16845; A61M 5/1415; A61M 2205/3553; A61M 2205/3569; A61M 2205/3592; A61M 2205/50; A61J 1/18; A61J 2200/74; A61J 2200/76; G01F 23/20; G08B 21/182
See application file for complete search history.

(56) References Cited

U.S. PATENT DOCUMENTS 5,394,866 A * 3/1995 Ritson ................. A61M 15/00
                                                128/200.14
9,140,596 B2 * 9/2015 Wang ..................... G01F 23/20
(Continued)

OTHER PUBLICATIONS

Smith & Nephew, Fluid Management, 2012, Levelert™ II Fluid Level Sensor, Reference #7211011, p. L-2.

*Primary Examiner* — Joseph Feild
*Assistant Examiner* — Rufus Point
(74) *Attorney, Agent, or Firm* — Peter Gutenberg, Esq.

(57) ABSTRACT

A fluid level monitoring device and a method of use are disclosed for alerting a user that the fluid in a container, such as an intravenous (i.v.) injection or irrigation bag or collection of waste from a human body (catheter) have reached a pre-determined volume.

6 Claims, 10 Drawing Sheets

(56) References Cited

U.S. PATENT DOCUMENTS

| | | | | |
|---|---|---|---|---|
| D752,464 S * | 3/2016 | Harmon | ........................ | D10/96 |
| 9,272,086 B2 * | 3/2016 | Williams | ............ | A61M 1/0058 |
| 9,474,848 B2 * | 10/2016 | Williams | ............ | A61M 3/0229 |
| 2003/0048185 A1 * | 3/2003 | Citrenbaum | ...... | A61M 5/16895 |
| | | | | 340/540 |
| 2008/0027409 A1 * | 1/2008 | Rudko | ................... | A61B 5/201 |
| | | | | 604/503 |
| 2008/0221512 A1 * | 9/2008 | Da Silva | ................. | A61B 5/20 |
| | | | | 604/65 |
| 2009/0126483 A1 * | 5/2009 | Blendinger | ........... | G01F 23/246 |
| | | | | 73/304 C |
| 2010/0228222 A1 * | 9/2010 | Williams | ............ | A61M 1/0058 |
| | | | | 604/500 |
| 2010/0228224 A1 * | 9/2010 | Pyles | ................. | A61M 1/0058 |
| | | | | 604/500 |
| 2011/0128152 A1 * | 6/2011 | Bregeon | .............. | A61G 7/0503 |
| | | | | 340/603 |
| 2015/0061876 A1 * | 3/2015 | Chang | ............... | A61M 5/16845 |
| | | | | 340/613 |
| 2015/0258277 A1 * | 9/2015 | Halpert | ............... | A61M 5/1723 |
| | | | | 604/503 |
| 2017/0109996 A1 * | 4/2017 | St. Germain | ........ | G08B 21/182 |

\* cited by examiner

FLUID LEVEL MONITORING SYSTEM

CROSS-REFERENCE TO RELATED APPLICATION

This application claims the benefit of Patent Cooperation Treaty application number PCT/US2015/014928, filed 6 Feb. 2015, which in turn claims the benefit of U.S. application No. 61/937,963, filed 10 Feb. 2014 and which are incorporated herein by reference.

BACKGROUND OF THE INVENTION

Disposable containers are used in many industries to hold and dispense fluids of various natures. When the fluid has been used and the container is empty, or when it is filled with waste, it is usually thrown away. Some examples of this type of packaging are flexible plastic i.v., catheter and irrigation bags commonly used in hospitals.

Sterile i.v. bags are normally used to dispense plasma, whole blood, replacement electrolyte, etc. The bags are usually imprinted or screen-labelled with the required documentation to identify the contents. When using containers of the i.v. bag type, the normal procedure is to dispense a metered amount over a given period of time by unmonitored, gravity-fed, drip feeding. The containers themselves come in different sizes, and i.v. fluids are administered to patients requiring widely varying flow rates. For example, 250 milliliter (ml.) to 3 liter plastic i.v. bags or bottles may be used to dispense a solution of 0.9% saline, Ringers lactate, 5% glucose, plasma, or blood to an adult over a 10-40 minute or longer time period, at rates of 1-25 ml. per minute (or more depending on the need).

It is a common practice to pre-set the gravity-driven flow rates via a visual drop-counting metering mechanism located above the i.v. catheter. However, pre-set flow rates can vary over a substantial range, due to changing resistance to outflow resulting from several variables. Some of the variables that can affect the flow rate include: the changing height of the insertion site relative to the fluid level as the patient moves about; a partial or complete closing (kinking) of the tubing; the thrombosis (clotting) promoting propensities of the solution being dispensed; the angle of the needle influencing the occlusion of its beveled opening; the settling of the various components of the fluid in the container, such as blood cells; and other reasons. In a chaotic environment such as an operating or emergency room, it is not always possible for someone to constantly monitor the amount of fluid in an i.v. bag.

It is detrimental to a patient to have the flow of an i.v. fluid come to a complete stop. Complications which can occur after the flow has stopped include the clogging of the needle due to blood clotting, usually requiring reinsertion of a new needle, or blood passing out of the patient into the tubing. It is important to note that, in addition to pain, the risk of infection and hematoma increases every time a needle has to be inserted and reinserted into a vein. In a high stress environment such as a hospital operating room or trauma center, staffs are often engaged in a variety of vital tasks at one time and the fluid levels of i.v. bags are often not changed, resulting in harm to the patient.

This contributes to the rise in healthcare costs, as patients require more care; while physicians and medical facilities are forced to payout large sums of money in medical malpractice lawsuits.

Similarly, many endoscopic surgeries, require that the bodily cavity be irrigated with a saline or similar solution. These irrigation solutions are delivered through a container, similar to an i.v. bag. Failure to monitor the bag may result in injury to the patient; for example, failure to maintain irrigation pressure, during a bladder surgery may result in a collapse of the compartment, causing the surgeon to lose track of the area he was working on or even cause inadvertent injury to the urethral orifices or puncturing the bladder cavity.

Operating room nurses and technicians currently have the responsibility for monitoring i.v. fluid levels and making sure they do not run out. However, in a busy operating room environment there are many distractions and demands for attention increasing the likelihood of an i.v. fluid inadvertently running out. A need, therefore, exists to find a practical, low-cost solution to the problem of how to determine, without constant direct human observation, when the fluid in one of these containers reaches a level requiring action by the nurse, doctor, attendant, or patient, and to get their attention at the required time. The present invention fills this need.

SUMMARY OF THE INVENTION

A primary object of the present invention is to provide the medical profession with an efficient, inexpensive way to continuously monitor the fluid levels in bags used for dispensing an i.v. or irrigation fluid or for collecting body fluids and alert the user when the fluid levels reach a pre-set weight.

The present invention provides a weight sensing fluid level monitoring system for determining when the amount of fluid in a container, for example, a disposable plastic bag used for intravenous infusion or the collection of biological fluids or other waste from a human body has reached a point where the container must be replaced or emptied. The device in its various embodiments can provide both visual and audible alarms at the patient's bedside or wirelessly transmit the alarm to a remote location, such as a nurse's station, by way of the internet or intranet.

The device is pre-programmed to alert the user when the weight of fluid in a container, such as an i.v., irrigation or catheter bag, reaches a certain pre-programmed level. The device is suspended between an i.v. stand or hook and a container, by way of top and bottom hooks projecting from the device. Internally, the hooks are attached to one or multiple strain gauges, which detect deformations in the hook members, caused by the weight of the container. It then transmits that information to a microprocessor by way of an analogue to digital converter. As the fluid in the container reaches its pre-programmed weight, the microprocessor triggers visual and audible alarms to notify the user that the container bag must be replaced.

In one embodiment, when the user sets the device with the container fluid amount and alarm threshold level. When the fluid level in the container decreases to a pre-determined level, the visual and audible alarms activate to notify the user that the level is becoming critically low. In another embodiment, when the fluid level in a bag collecting body fluids rises to a pre-determined level, the visual and audible alarms activate to notify the user that the level is becoming critically high.

In a further embodiment, the device contains a wireless transmitter for connection to the internet. When the fluid reaches its pre-programmed level, an alarm will be triggered at a remote location, (e.g., a nurse's station).

In yet another embodiment of the device, the device is pre-programmed with, its location in the medical facility, the fluid that it is monitoring, the amount of fluid in the container, and the alarm threshold. When the threshold fluid level is reached, the device, through the wireless transmitter notifies a medical facility's automated inventory system that the container must be changed. The automated inventory system, in turn, alerts the supply room to bring a new container to the device's pre-programmed location and sends an acknowledgement back to the device so it may let the operating room staff know that more material is on the way Thus, the present invention in its different embodiments provides an easy-to-use, inexpensive, portable fluid level monitoring device which can be installed in every hospital room, ambulance, or mobile medical facility. The immediate advantages of using such a fluid level monitor would include reducing the incidence of injury to patients caused by failure to timely change the i.v. or catheter bag and increasing productivity for the medical professionals by not having to continuously monitor fluid levels. Furthermore, the energy source necessary to power this device is self-contained, in the form of readily available batter(ies), making the device completely portable.

BRIEF DESCRIPTION OF THE DRAWINGS

These and other objects, features, and aspects of the invention will be better understood and more fully described upon reading the following detailed description in conjunction with the appended drawings wherein.

DETAILED DESCRIPTION

Figure 1:
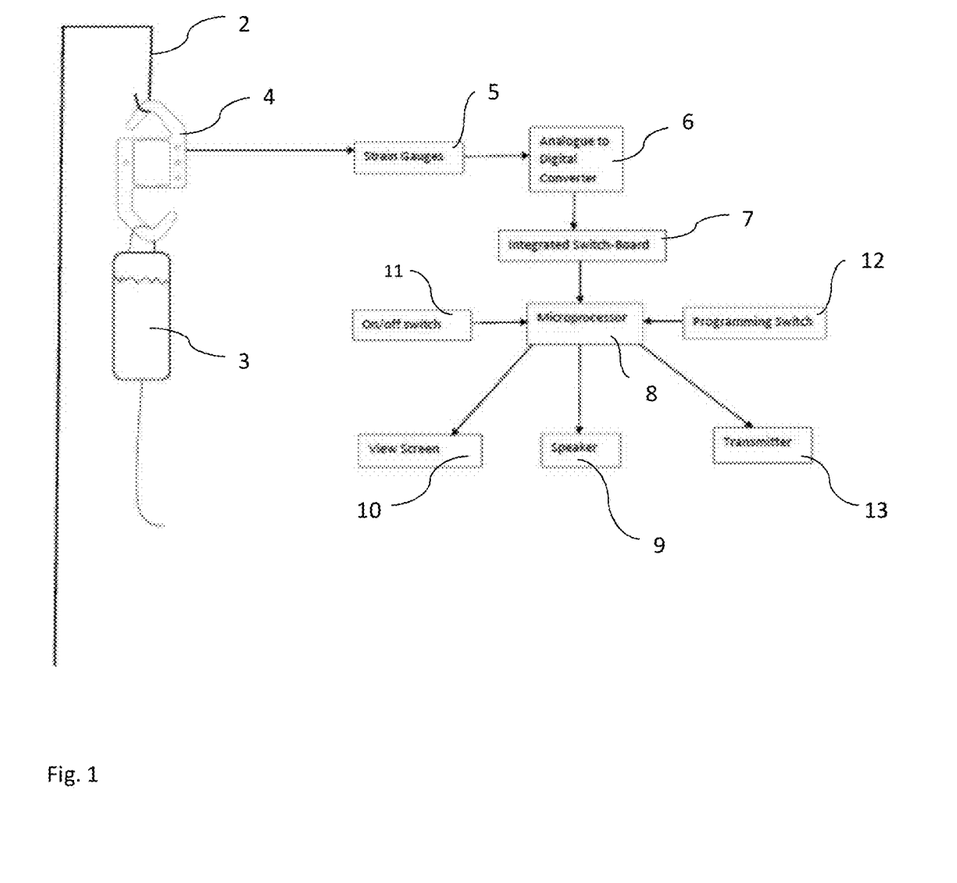
FIG. 1 is a block diagram of a system for determining the fluid level in container in accordance with the present invention.

Referring now to FIG. 1, depicting the operation of the preferred embodiment of a weight measuring fluid level monitoring device (hereinafter the "device) constructed in accordance with the present invention is shown. The device is suspended between a hook or i.v. stand 2 and a container 3, such as an i.v., irrigation or catheter bag, or bottle by a sensing assembly 4, with top and bottom hook members 19,20 comprised of a double bending hook member and four strain gauges 5. The four strain gauges 5 measure the distortions in the sensing assembly caused by the weight of the container and transmit that information to a microprocessor board 8 by way of a 24-bit sigma-delta analog-to-digital converter board 6 which is tightly integrated with the sensing elements and an integrated switch board 9. The microprocessor then signals a speaker to emit an audible alarm 9 and a view screen 10 to emit a visual alarm in the form of a flashing LED backlight. The device is activated through an on/off switch 11.

In the preferred embodiment, the tare is automatically set at the time the unit is first turned on. The user sets the initial alarm threshold using a momentary center-off programming switch 12. The threshold level is set based on the initial volume of fluid in the container; given that the fluid, such as saline, used in many medical uses has a density of approximately 1 gram per milliliter, weight and volume may be used interchangeably. The threshold value may be set for any value down to the milliliter. Alternative embodiments of the invention may tradeoff precision and accuracy of the measurement and alarm, or utilize a programming element in the form of a touch enabled view screen; USB-connected peripheral device, such as a tablet or smartphone; or from a remote location by way of an internet enabled, wireless transmitter 13

While the preferred embodiment of this device utilizes a four strain gauge configuration, alternative embodiments may utilize one or two strain gauge configuration, with tradeoffs in cost, dynamic range, sensitivity, accuracy and/or precision.

A one or two strain gage system may be created either by simply mounting only one or two strain gages on the existing double bending beam configuration. Alternately, a simpler single beam mechanical configuration may be employed, with that mechanism becoming more susceptible to off-axis forces.

In another embodiment, the device contains a wireless transmitter for connection to the internet, allowing for notification of a remote location, such as a nurse's station or connecting to a medical facility's store room.

Figure 2:
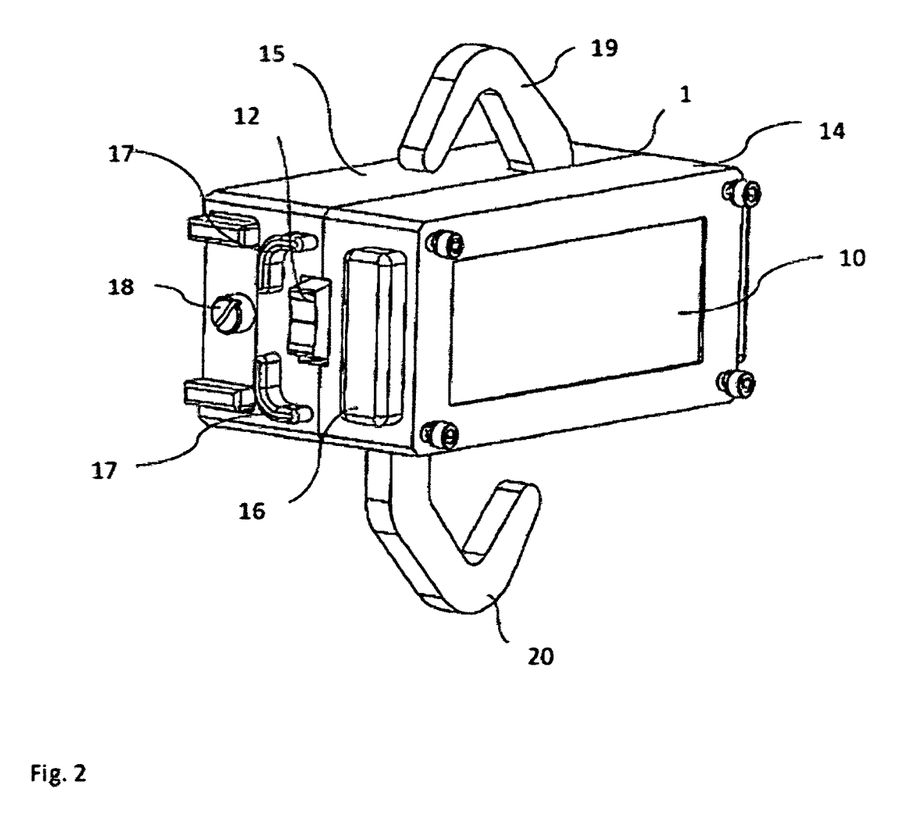
FIG. 2 is a left perspective view of the preferred embodiment of a fluid level sensor.

FIG. 2 illustrates a left perspective view of the device 1. The housing consists of front and rear assemblies 14, 15. The alarm threshold is set by a momentary center-off programming switch 12. Guard fences, located front and rear of the momentary center-off switch 16, 17, provide protection from damage, such as a from a drop. A stainless steel captive thumbscrew 18 is used to secure the rear battery compartment cover to the device. Top and bottom hook members 19, 20 of the sensing assembly can be seen protruding from the top and bottom of the device between the front and rear assemblies, the hook members are asymmetric and opposing one another; from this view, the top hook member is partially obscured.

Figure 3:
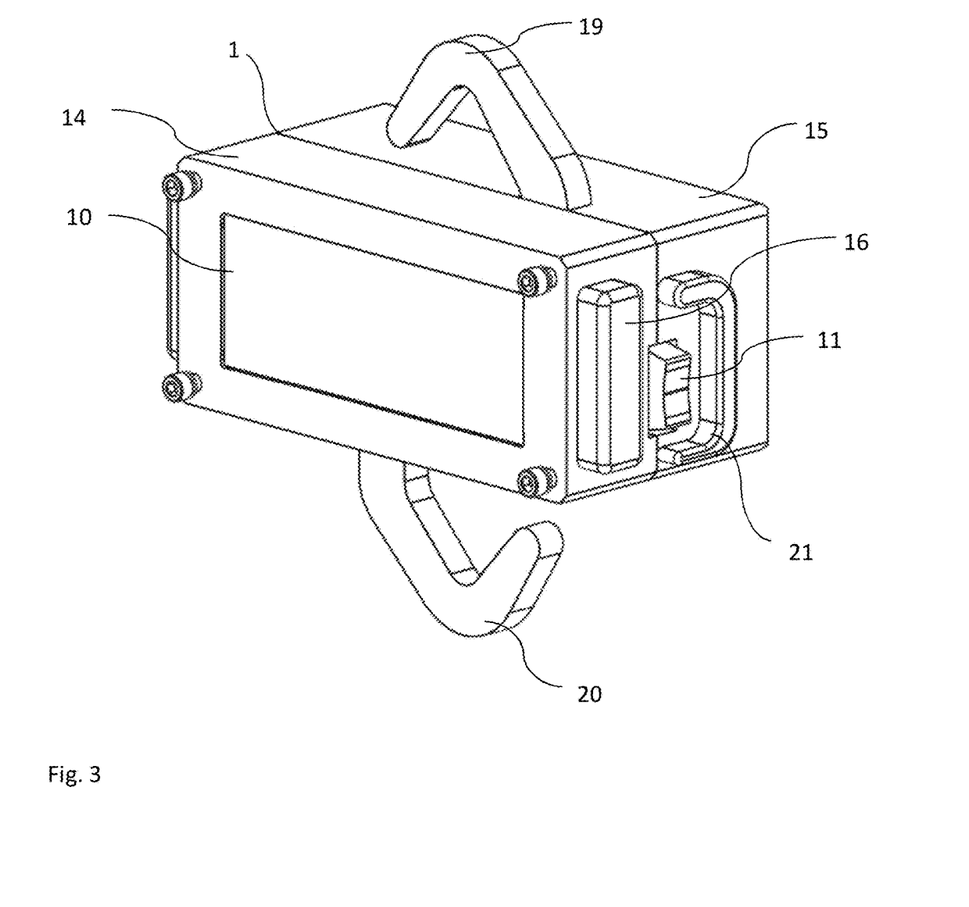
FIG. 3 is a right perspective view of the preferred embodiment of a fluid level sensor.

FIG. 3 illustrates a right perspective view of the device 1. The housing consists of front and rear assemblies 14, 15. The device is activated by an on/off switch 11. Guard fences 16, 21, located front and rear of the programming switch provide protection from damage, such as from a drop. A stainless steel captive thumbscrew 18 is used to secure the rear battery compartment cover to the device. Top and bottom hook members 19, 20 of the sensing assembly can be seen protruding from the top and bottom of the device between the front and rear assemblies, the hook members are asymmetric and opposing one another; from this view, the top hook member is partially obscured.

Figure 4:
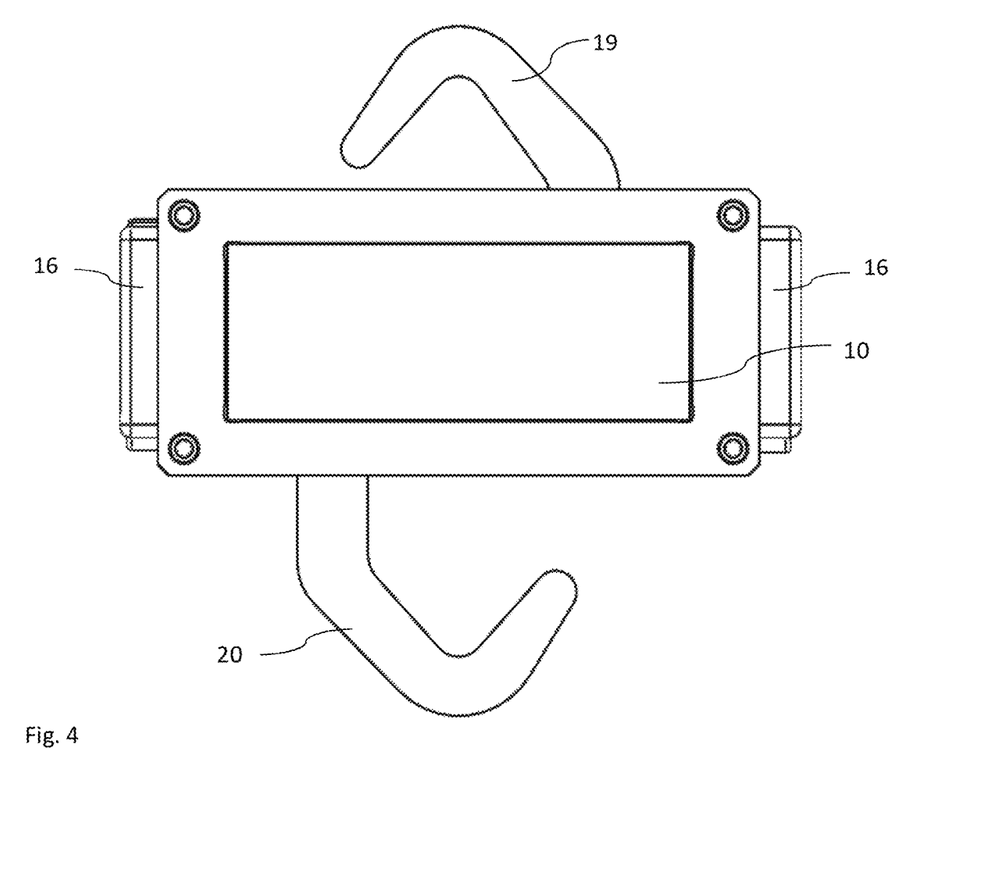
FIG. 4 is a front view of the preferred embodiment of a fluid level sensor.

FIG. 4 illustrates a frontal view of the device. From this view the asymmetric and opposing placement of the top and bottom hook members 19, 20 is apparent. In the preferred embodiment, the view screen 10 supports a 2-line alphanumeric display, with up to 16 characters per line, red, green, or blue LED status dependent backlighting which blinks, and then flashes as fluid level goes below pre-programmed threshold level. The top line displays approximate fluid remaining; the bottom line displays alarm threshold or other messages as appropriate. Alternative embodiments, may support another display type, such as a touch screen enabled liquid crystal display.

Figure 5:
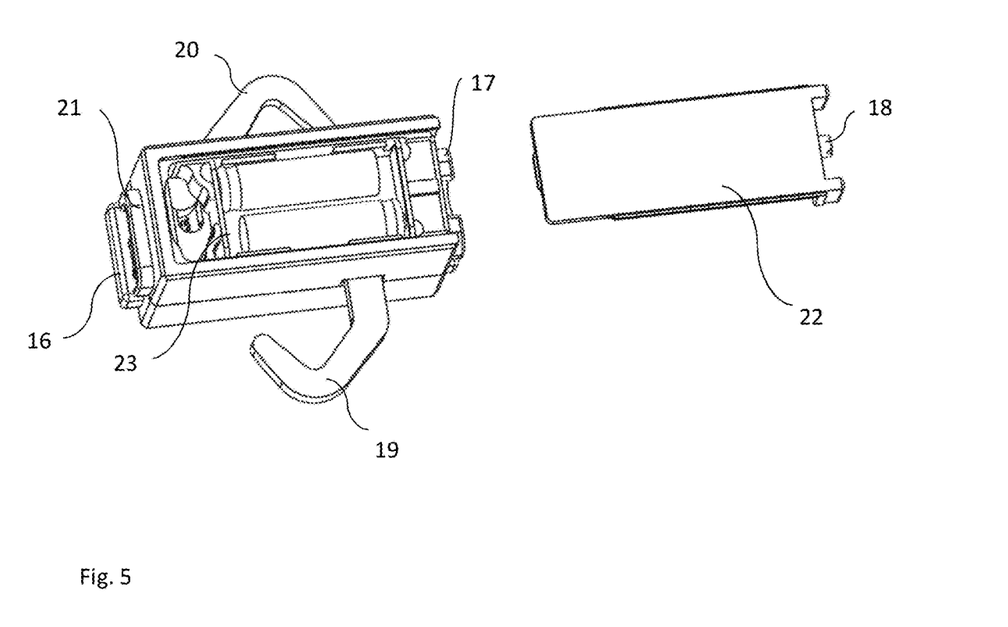
FIG. 5 is a rear perspective view of the preferred embodiment of a fluid level sensor with the battery cover removed.

FIG. 5 illustrates a rear perspective view of the preferred embodiment of the device with the battery compartment cover 22 removed, exposing the battery compartment 23; the stainless steel captive thumbscrew 18 is used to secure the battery compartment cover to the device and stays with the battery case cover when it is removed from the body of the device. In the preferred embodiment, commercially available AA batteries are used as a power source; though other embodiments may utilize other battery types, such as AAA, 9 V or a lithium ion battery.

Figure 6:
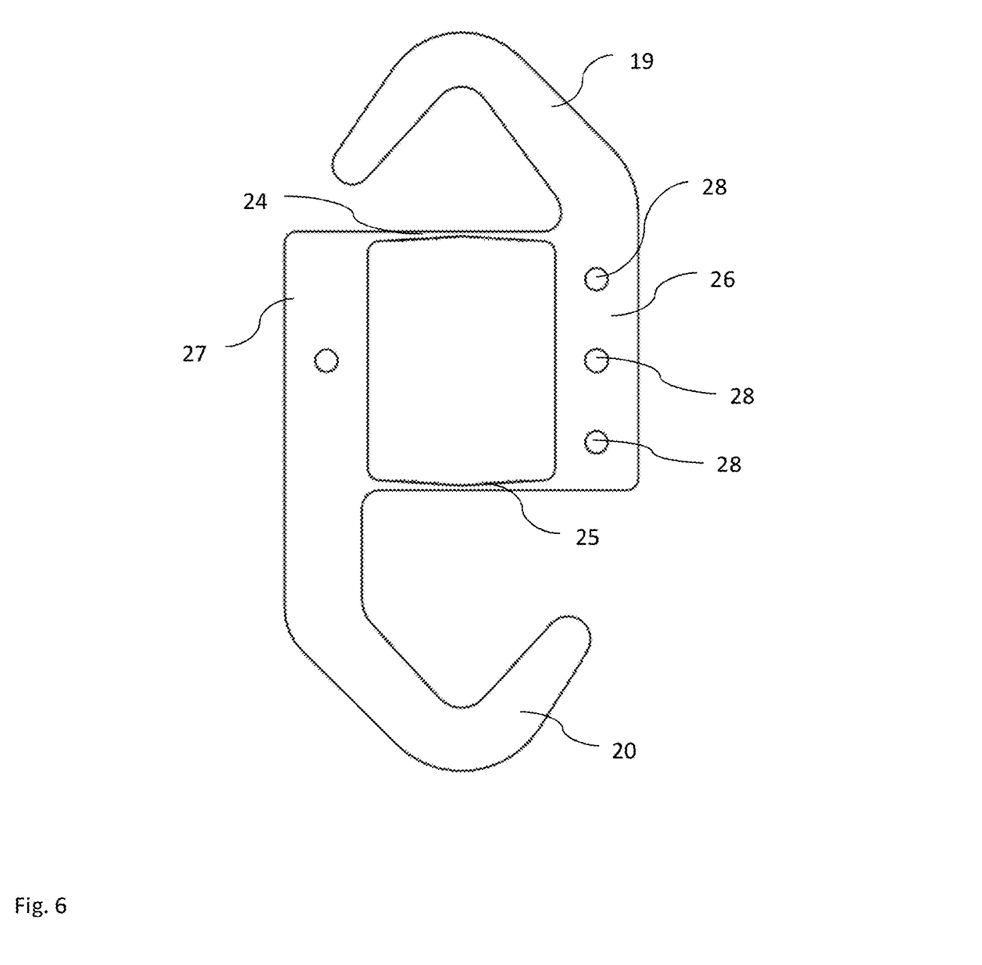
FIG. 6 is a front view, of the preferred embodiment of the sensing assembly of the fluid level sensor.

FIG. 6 illustrates a front view of the sensing assembly. The sensing assembly 4 is composed of a double bending hook member constructed of a single piece of aluminum, though other metals or materials may be used. The double bending hook member is further comprised of a rectangular member and two hook members. The rectangular member is composed of top and bottom horizontal legs 24, 25; right and left vertical legs, 26, 27. The vertical legs are thick, relative to the horizontal legs and form the top and bottom hook members 19, 20 which couple the load to the horizontal legs 24, 25. The top and bottom hook members 19, 20 protrude outward from their respective vertical legs, through the housing and are situated so that they are asymmetric and opposing to one another. The top hook member 19 is suspended from a hook or i.v. stand 2 and the load, the fluid container, is attached to the bottom hook member 20. One vertical leg 26 contains holes 28 for attachment directly to the housing. The configuration of the sensing assembly 4 in a dual bending beam configuration with the two bending beams, the top and bottom horizontal legs 24, 25, widely separated; naturally resists torsional and off-axis forces from affecting a reading.

Figure 7:
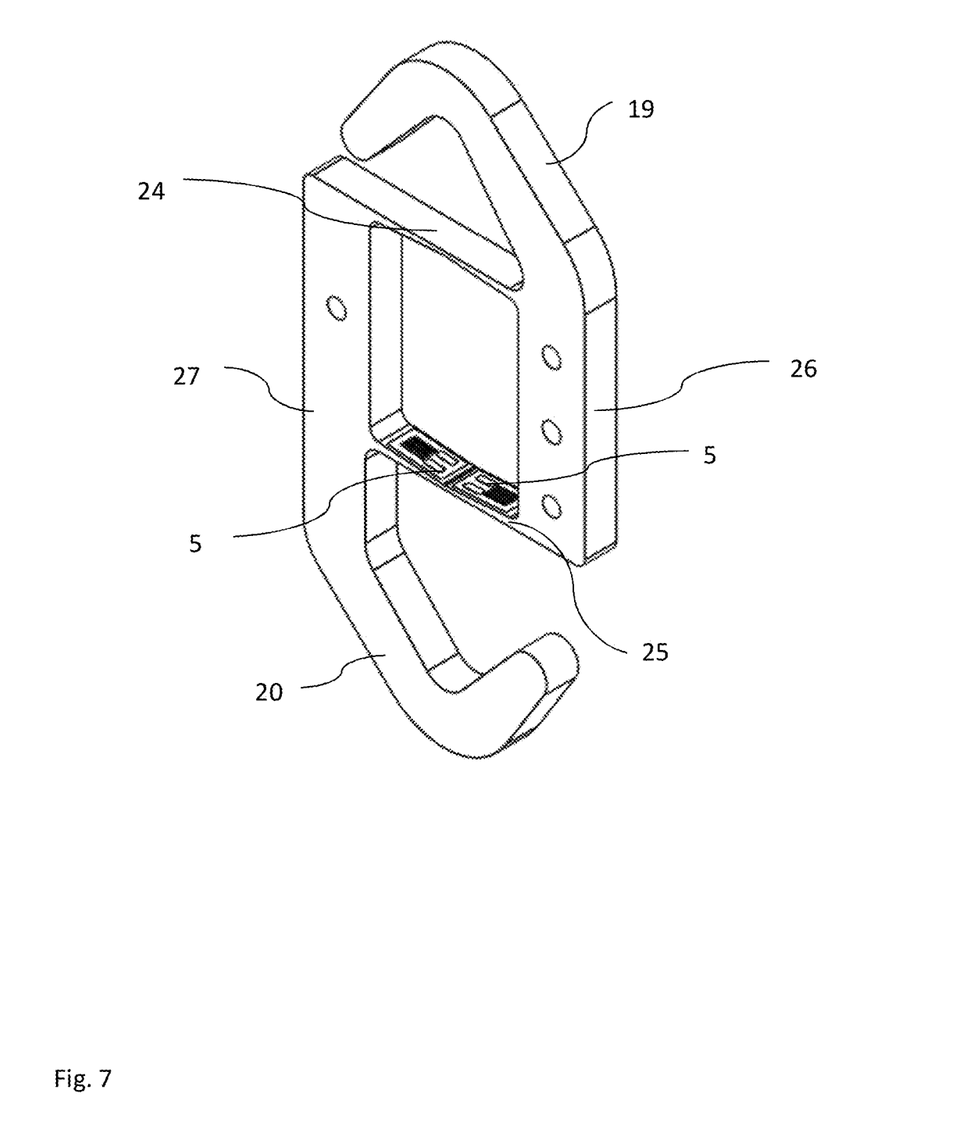
FIG. 7 is a right, top perspective view of the preferred embodiment of the sensing assembly of the fluid level sensor.

FIG. 7 illustrates a right, top perspective view of the sensing assembly. The centers of the two horizontal legs, 24 and 25 are hollowed out and tapered with the thinnest section at the center so the mechanical strain is more uniformly distributed across the area of the beam, this allows them to become the bending beams for the load cell; this also serves to improve the efficiency of the strain gauges. The four strain gauges 5 of the preferred embodiment, each the width of the rectangular member are placed along the horizontal legs, one at each corner of the rectangular member. Each horizontal member contains two strain gauges 5, one to measure compression, while the other strain gauge measures tension. Alternative embodiments of the invention may utilize a two strain gauge configuration, wherein both strain gauge are placed along either the top or bottom horizontal leg; or a one strain gauge configuration where a single strain gauge is placed along ether the top or bottom horizontal leg.

Figure 8:
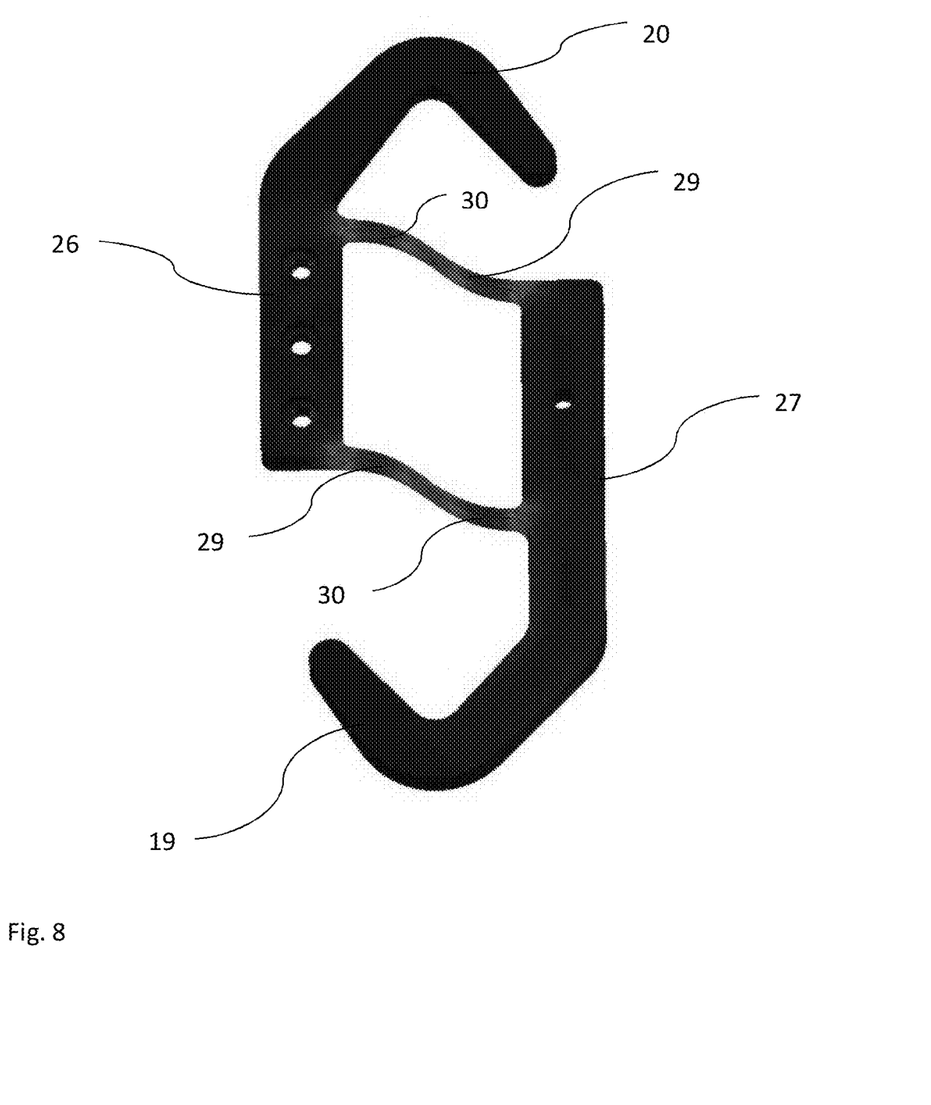
FIG. 8 is a front perspective view of the preferred embodiment of the sensing assembly of the fluid level sensor under stress.

FIG. 8 illustrates the sensing assembly while under a weight load bearing stress. While supporting weight, the interior surface of the bending beam where the strain gauges are mounted, half of a single horizontal member is in tension 29, and the other half is in compression 30, causing the horizontal member to bend in a sigmoidal shape due to the orientation of the hooks. By utilizing two strain gauges in each bending arm, a Wheatstone bridge is formed.

Figure 9:
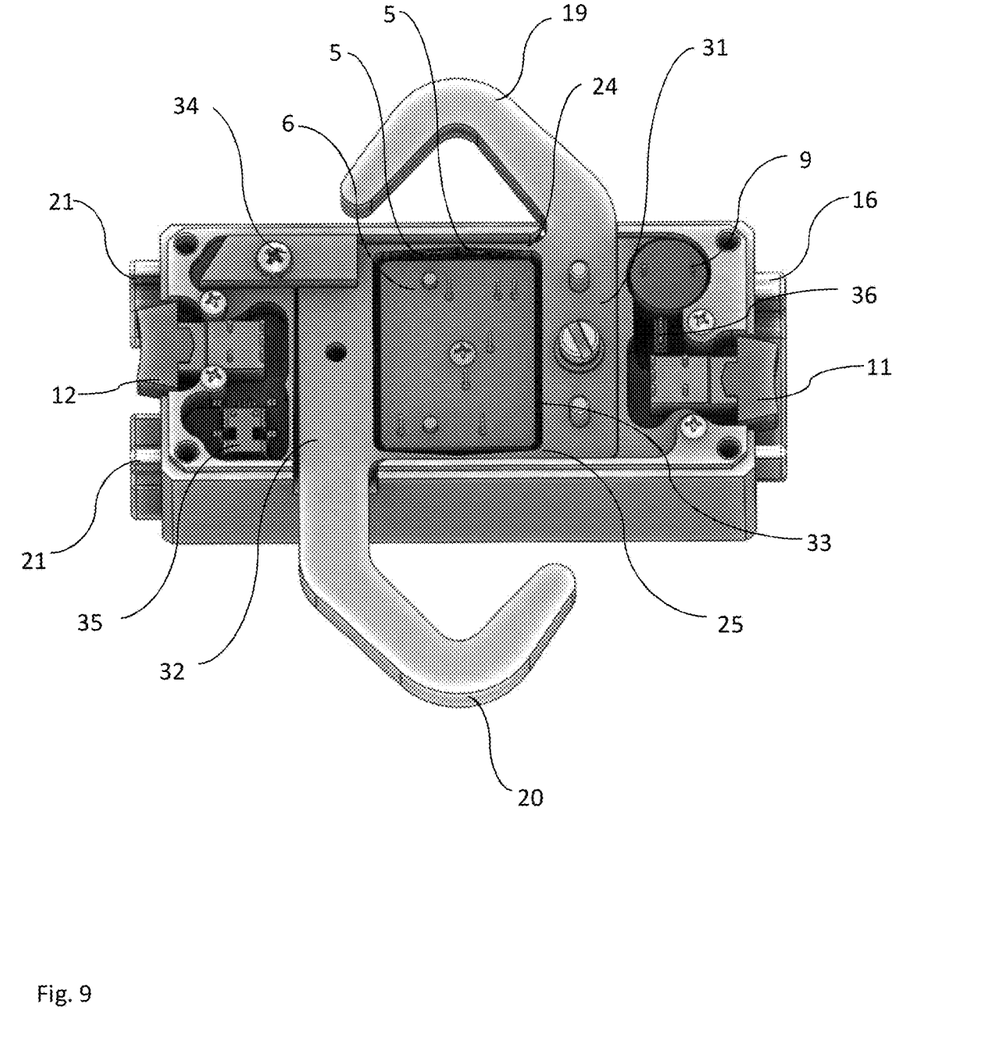
FIG. 9 is a front perspective view, of the preferred embodiment of a fluid level sensor with the front casing, view screen, and microprocessor board removed.

FIG. 9 illustrates a front perspective view of the device with front housing assembly 14, including the view screen 10 and microprocessor board 8, and switch-interface board 7, removed. In the preferred embodiment, strain from the weight of a container 3 suspended from the bottom hook 20 of the sensing assembly is measured by a series of four strain gauges 5 in a Wheatstone bridge configuration.

One of the vertical legs 31 is attached directly to the housing; while the other vertical leg 32 and both horizontal legs 24, 25 are free floating inside the enclosure; this allows for free movement of the bending beams and the lower hook, while under load. The analogue to digital converter 6 sits at the center of the rectangular member. The analogue to digital converter is connected by soldered wires, not shown, to each strain gauge 5.

The rear housing 20 has a precision cavity 33 machined into it to accommodate the rectangular member of the sensing assembly and allow for the hook members to protrude from the top and bottom. Under the current embodiment, the aluminum bending beams are capable of supporting an object of up to 30 pounds weight or 57,200 psi of force, before the bending beams reach their elastic limit of 0.055" of displacement. The clearance between the horizontal legs of the sensing assembly and the housing is less than 0.05", therefore preventing deformation of the bending beams before the elastic limit is reached. This allows for sufficient deflection on the horizontal legs, less than would be required for permanent elastic deformation under high stress or fault conditions, such as being dropped, yet enough so that linear operation through the intended stress range is allowed.

According to the preferred embodiment of the device, the sensing assembly is able to detect changes in the weight down to one-tenth of a milliliter or gram; however in practice, the device will be set down to the milliliter or gram level; with the lowest available threshold alarm setting at approximately 50 mL or g.

When fluid levels drop to a pre-programmed level, the strain on the horizontal legs of the rectangular member will lessen, that loss of strain will be measured by the strain gauges which will then transmit that loss of strain through the analogue to digital converter and on to the microprocessor board; the microprocessor board will then activate both a visual alarm, and sound an audio alarm. Both alarms will continue until the fluid level monitoring device is shut-off, re-set by the user, or a new bag is hung.

Also illustrated in FIG. 9 are a retention bar 34, the speaker 9, a USB connector 35, and a feed through 35 to the battery compartment. The placement of the retention bar allows for drop protection. The USB connector allows for pre-programming from a personal computer, or a mobile device such as a tablet or smartphone.

Figure 10:
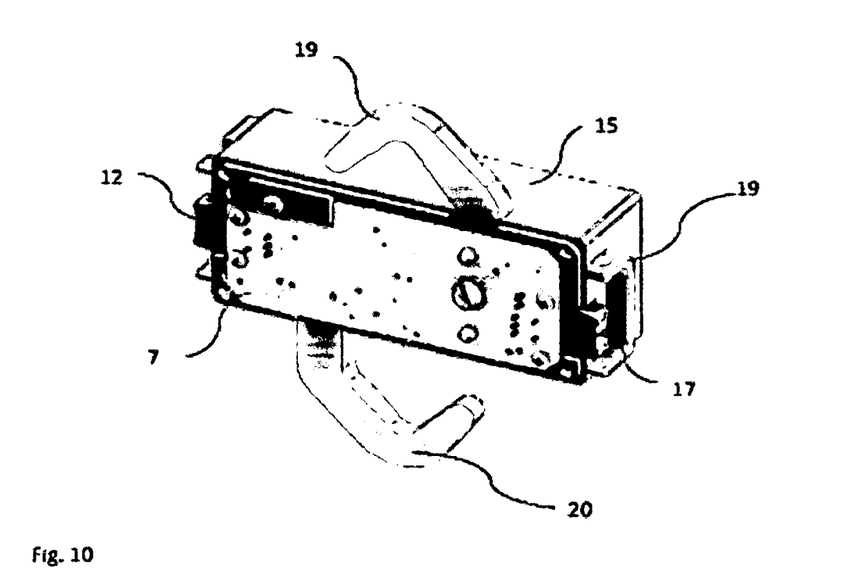
FIG. 10 is a front perspective view of the preferred embodiment of a fluid level sensor with the front of the housing, view screen and microprocessor removed.

FIG. 10 illustrates a front perspective view of the device with the front housing, including view screen 10, and microprocessor board 8 removed. The rear side of the switch-interface board 7 connects to the analog to digital converter board, while the microprocessor board connects to the front housing assembly. The switch-interface board also provides a mounting plane for the switches, the speaker, the USB connector, and a feed through connector to the battery compartment.

In an alternate embodiment of the device, the fluid level monitoring device has a wireless connection interface and is connected to a medical facility automatic ordering system through a wireless internet connection. Prior to use, the fluid level monitoring device is uniquely identified and pre-programmed with its location, the nature of the fluid it is monitoring, the initial volume or weight of the fluid container, and a threshold weight corresponding to a fluid volume which will trigger the alarms. When the pre-programmed alarm threshold is initially reached, the visual display flashes and the audible alarm sounds to notify the local user that the fluid level has reached its pre-programmed threshold. The device further transmits instructions to the medical facility's automatic ordering system that a new container is needed; in turn the automatic ordering system contacts the facility stock room and requests that a new container be brought to the fluid level monitoring device's location.

In review, it can now be seen that the fluid level monitoring device of the present invention provides an inexpensive, easy-to-use, self-contained device having numerous applications. Each of the various embodiments described above provide particular advantages in various applications of fluid level monitoring. An acknowledgement is sent back to the device. If an acknowledgement is not received by the time the fluid reaches a lower predetermined level the device will alarm again, indicating personal intervention is needed While preferred embodiments of the invention have been illustrated, it will be obvious to those skilled in the art that various modifications and changes may be made thereto without departing from the spirit and scope of the invention as hereinafter defined in the appended claims.

We claim:

1. A device for monitoring fluid levels comprising: housing with a front assembly and a rear assembly; a sensing assembly, an analog to digital converter; wherein the sensing assembly comprises a rectangular member, with a top horizontal leg, a bottom horizontal leg, a left vertical leg, a right vertical leg, a bottom hook projecting from the left vertical leg out of said housing; a top hook projecting from the right vertical leg out of said housing, up to four strain gauges; wherein the top and bottom horizontal legs are tapered and hollow at their centers; wherein the top and bottom hooks oppose each other and are planar to the rectangular member; wherein the one vertical leg is attached to the housing and the left vertical leg, and the top and bottom horizontal legs are free floating; wherein the up to four strain gauges are arranged along the horizontal legs; wherein the up to four strain gauges are connected to the analogue to digital converter; wherein the analogue to digital converter, a speaker, a view screen, a programming switch, an on/off switch, and a wireless transmitter are connected to a microprocessor; wherein a power source is connected to the microprocessor; wherein said strain gauges detect deformations in the rectangular member caused by suspension of a weighted object from the bottom hook member and communicate the detected deformations through the analogue to digital converter to the microprocessor; wherein the programming switch, or a peripheral device connected to the device, either through a peripheral port or wirelessly is used to set an initial weight or volume and/or a threshold value; wherein when the threshold value is reached, the microprocessor activates the speaker, causing the speaker to emit an audible alarm and causes the view screen to indicate a visual alarm; wherein the view screen is attached to and visible through the front assembly indicating a status back light in either red or green color, each color corresponding to low or filled fluid levels, respectively; wherein the status back light blinks and flashes once the threshold value is met and passed; wherein the wireless transmitter notifies a remote location once threshold value has been met or exceeded.

2. A device according to claim 1, comprising exactly four strain gauges, wherein said strain gauges are placed along the horizontal legs, one adjacent to each corner of the rectangular Member.

3. A device according to claim 1, comprising exactly two strain gauges, wherein both said strain gauges are placed along either the top or bottom horizontal legs.

4. A device according to claim 1, comprising exactly one strain gauge, wherein said strain gauge is placed along either the top or bottom horizontal legs.

5. A method of monitoring fluid levels in a container using a device for monitoring fluid levels according to claim 1; wherein the device is programmed with its location through a peripheral device; wherein the wireless transmitter notifies a remote station once the threshold level has been met or surpassed; wherein said remote station deactivates the alarm.

6. A method of monitoring fluid levels in a container using a device for monitoring fluid levels according to claim 1; wherein the device is programmed with its location through a peripheral device; wherein the wireless transmitter notifies a remote station once the threshold level has been met or surpassed; wherein said remote station is notified to bring a replacement container to said device location.

* * * * *